(12) United States Patent
Herbst et al.

(10) Patent No.: US 10,406,518 B2
(45) Date of Patent: Sep. 10, 2019

(54) DEVICE AND METHOD FOR STORING AND TRANSPORTING A BODILY FLUID SAMPLE

(71) Applicant: EUROIMMUN MEDIZINISCHE LABORDIAGNOSTIKA AG, Lübeck (DE)

(72) Inventors: Victor Herbst, Krummesse (DE); Birgit Nagel, Lübeck (DE)

(73) Assignee: EUROIMMUN MEDIZINISCHE LABORDIAGNOSTIKA AG, Lübeck (DE)

(*) Notice: Subject to any disclaimer, the term of this patent is extended or adjusted under 35 U.S.C. 154(b) by 312 days.

(21) Appl. No.: 14/900,360

(22) PCT Filed: Jun. 11, 2014

(86) PCT No.: PCT/EP2014/001583
§ 371 (c)(1),
(2) Date: Dec. 21, 2015

(87) PCT Pub. No.: WO2014/206531
PCT Pub. Date: Dec. 31, 2014

(65) Prior Publication Data
US 2016/0151780 A1 Jun. 2, 2016

(30) Foreign Application Priority Data
Jun. 24, 2013 (DE) .......... 10 2013 211 918

(51) Int. Cl.
*B01L 3/00* (2006.01)
*A61B 10/00* (2006.01)

(52) U.S. Cl.
CPC ........ *B01L 3/5023* (2013.01); *A61B 10/0096* (2013.01); *B01L 3/5085* (2013.01);
(Continued)

(58) Field of Classification Search
CPC .. B01L 3/5023; B01L 3/5085; B01L 2200/18; B01L 2200/0605; B01L 2200/10;
(Continued)

(56) References Cited

U.S. PATENT DOCUMENTS 3,162,306 A 12/1964 Zackheim
3,996,006 A 12/1976 Pagano
(Continued)

FOREIGN PATENT DOCUMENTS

| EP | 2 420 831 A1 | 2/2012 |
| WO | 00/54029 A1 | 9/2000 |
| WO | 2006/034592 A1 | 4/2006 |

OTHER PUBLICATIONS

Li et al., "Perforated dried blood spots: a novel format for accurate microsampling," *Bioanalysis* 3(20):2321-2333 (2011).
(Continued)

*Primary Examiner* — Dennis White
(74) *Attorney, Agent, or Firm* — Seed IP Law Group LLP

(57) ABSTRACT

The invention relates to a device and to a method for storing and transporting a bodily fluid sample, comprising a support element (2), which forms a main body. At least one sorption element (3), which has a defined filling volume and is suitable for receiving a drop of the bodily fluid, and an overflow reservoir (4), which is adjacent to the sorption element (3) and which receives the bodily fluid from the sorption element (3) as soon as the filling volume of the sorption element (3) is filled, are fastened to the support element. The technical solution according to the invention is characterized in that at least one predetermined breaking point (5) is provided, which is designed in such a way that the sorption element (3) can be manually detached from the support element (1) and/or from the overflow reservoir (4) without an auxiliary tool.

16 Claims, 3 Drawing Sheets

(52) U.S. Cl.
CPC ... *B01L 2200/0605* (2013.01); *B01L 2200/10* (2013.01); *B01L 2200/18* (2013.01); *B01L 2200/185* (2013.01); *B01L 2300/021* (2013.01); *B01L 2300/069* (2013.01); *B01L 2300/0681* (2013.01); *B01L 2300/0816* (2013.01); *B01L 2300/0829* (2013.01)

(58) Field of Classification Search
CPC ..... B01L 2300/0829; B01L 2300/0681; B01L 2300/069; B01L 2300/0816; B01L 2200/185; B01L 2300/021; A61B 10/0096
See application file for complete search history.

(56) References Cited

U.S. PATENT DOCUMENTS

| | | | |
|---|---|---|---|
| 5,100,619 A * | 3/1992 | Baker | B01L 3/5055 422/408 |
| 5,683,915 A | 11/1997 | Black et al. | |
| 5,895,704 A * | 4/1999 | Lerch | A61B 10/0096 422/411 |
| 5,939,259 A | 8/1999 | Harvey et al. | |
| 2013/0143226 A1 | 6/2013 | Hill et al. | |

OTHER PUBLICATIONS

Li et al., "Perforated dried blood spot accurate microsampling: the concept and its applications in toxicokinetic sample collection," *Journal of Mass Spectrometry*, Special Feature: Tutorial (wileyonlinelibrary.com) DOI 10.1002/jms.3015 (14 pages) (Accepted Apr. 23, 2012).

Chinese Office Action for related application No. CN 201490000960. 1, 5 pages, with English translation, dated Jun. 8, 2016.

German Office Action for related application No. DE 102013211918. 6, 8 pages, with English translation, dated Sep. 30, 2013.

International Preliminary Report on Patentability, 24 pages, with English translation, dated Jan. 7, 2016.

* cited by examiner

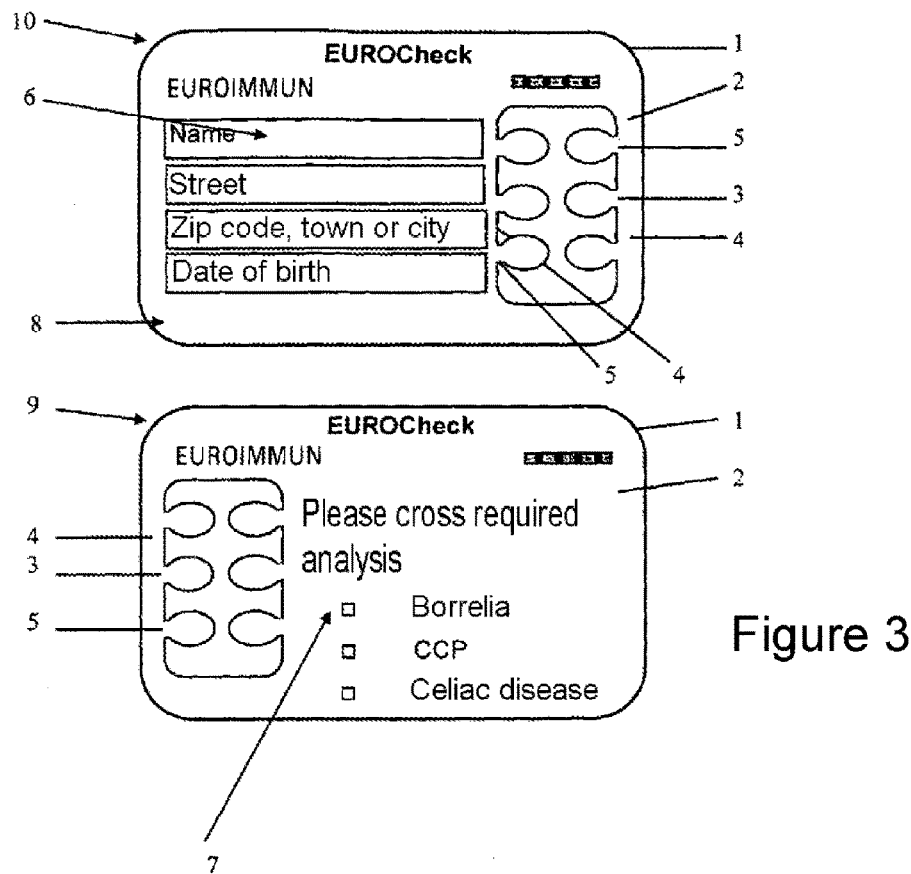
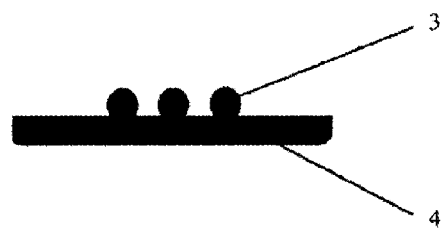
Figure 4

DEVICE AND METHOD FOR STORING AND TRANSPORTING A BODILY FLUID SAMPLE

The invention relates to a device and a method for storing and transporting a bodily fluid sample from a sampling site to the laboratory, optionally also for processing the sample. The device has as its main components a support element, which forms a main body, at least one sorption element for receiving a fluid sample, and an overflow reservoir adjacent to the sorption element. The sorption element has a defined filling volume for receiving a drop of a bodily fluid that is to be tested. As soon as the sorption element is filled completely with sample fluid, excess fluid is taken up by the adjacent overflow reservoir.

In the field of in vitro diagnostics, tests are generally known in which a drop of blood is taken from a patient, is then dropped onto a filter paper field provided for this purpose on a test card and is sent with the card to a laboratory. To be able to test the patient's blood sample in a suitable way in the laboratory, the fields provided with the blood are usually first of all punched out with the aid of a punch.

The aforementioned tests are mainly used for screening, in particular for screening of neonates. In this connection, the main test known is the Guthrie test, which was developed in the early 1960s by Robert Guthrie. In this test, blood taken from the heel of a neonate is dropped onto fields provided for this purpose on a filter paper card and, after it has dried, is sent to a laboratory. There, disks of a defined size are punched out from the areas that had been incubated with a drop of blood, and they are applied to a nutrient base, which is provided with the biological materials needed for the test.

The known methods are mainly characterized by the fact that the blood sample can be taken from the patient in a comparatively simple way, only a very small amount of blood is needed, and the patient's sample can be sent in a relatively uncomplicated way to a laboratory.

EP 2 420 831 A discloses a test card with a test field onto which patient samples can be applied in the form of drops. An essential feature of the technical solution described in said document is that a recess is provided in the interior of the test card, into which recess a filter paper for receiving the blood sample is clamped. A special filter paper, namely so-called glass fiber paper, is used here in order to avoid a situation where the blood sample runs out of the areas provided for the purpose into surrounding areas. This is intended to permit a precise analysis of small molecules too.

Proceeding from the known test cards, the so-called filter paper cards or dry blotting tests in which the required sample area always has to be punched out in the laboratory with the aid of a punching tool prior to testing the blood sample, the object of the invention is to develop a device and a method in such a way that the sampling procedure and the transport of the patient's sample can take place in a comparatively simple way and, at the same time, the processing of the sample in the laboratory is simplified. In particular, the aim is, on the one hand, to simplify the handling of the individual filter paper cards and, on the other hand, to minimize the need for additional laboratory equipment.

The above object is achieved with a device as per claim 1 and with a method as per claim 8. Advantageous embodiments of the invention form the subject matter of the dependent claims and are explained in more detail in the following description with reference to the figures.

The invention first relates to a device for storing and transporting a bodily fluid sample, comprising a support element, which serves as a main body and on which are secured at least one sorption element and an overflow reservoir, which is adjacent to the sorption element. The sorption element has a defined filling volume and is suitable for receiving a drop of the bodily fluid. The overflow reservoir, which is adjacent to the sorption element, is moreover designed in such a way that it receives bodily fluid from the sorption element as soon as the filling volume of the sorption element is filled completely with bodily fluid. According to the invention, the device has been developed in such a way that at least one predetermined breaking point is provided, the latter being designed in such a way that the sorption element can be manually detached from the support element and/or from the overflow reservoir without an auxiliary tool.

The essential feature of the technical solution according to the invention is thus that the sorption element can be easily detached from the support element and/or from the overflow reservoir in the laboratory, in particular without an auxiliary tool. In the context of the invention, manually and without an auxiliary tool are to be understood as meaning that the predetermined breaking point is designed in such a way that the sorption element can be broken off from the support element and/or from the overflow reservoir exclusively by hand. It is important here that no additional device, in particular no punching device, is needed in order to detach the sorption element with the bodily fluid sample from the test device.

According to a first particular embodiment of the invention, provision is made that the at least one predetermined breaking point is situated between the overflow reservoir and the sorption element. Advantageously, provision can be made that an overflow reservoir is provided on or in the support element used as the main body of a test card, which overflow reservoir is in turn connected to at least one sorption element. The predetermined breaking point is in this case advantageously situated between the overflow reservoir and the sorption element. In a preferred embodiment, the expression a "predetermined breaking point", as used herein, is to be understood as a site which is of such a nature that a uniform bending along the longitudinal axis of the whole article causes a break to appear first at this site. For example, the predetermined breaking point can be produced by forming small slits in a layer of plastic which is bendable but not permanently deformable, preferably a layer of an elastomer. The layer is slit in a shape which is oriented along the profile of the desired aperture that results when the predetermined breaking point breaks. Depending on the required patient samples and/or on the tests to be carried out, at least two sorption elements, very particularly preferably a plurality of sorption elements, are provided on or in a test card, and these sorption elements are each in turn connected to an overflow reservoir, particularly preferably to a common overflow reservoir.

It is essential that the individual sorption elements have a defined filling volume, which is dimensioned according to how large the patient sample has to be in order to ensure high-quality testing of the sample. In a particular embodiment of the invention, the dimensioning of a sorption element also takes into account the fact that the latter has to be able to be inserted easily into a cup-shaped recess of a microtiter plate, i.e. into what is called a well, or has to be able to be applied to a bot strip. The great advantage in this case is that the individual sorption elements are not only easy to detach from the support element, in particular from a test card, manually without an auxiliary tool, but that they are also easy to process further in the laboratory. As soon as too much blood has been applied to the sorption element, i.e. an amount beyond the defined filling volume, the excess amount of the patient sample is automatically taken up by the overflow reservoir. In this context, according to a particular development, it is conceivable that the overflow reservoir has the same material as the sorption element.

According to another particular embodiment, the support element of the device designed according to the invention has at least one information field into which it is possible to enter information concerning the nature and/or origin of the bodily fluid sample and/or concerning a test to be carried out. Advantageously, special fields into which information can be entered concerning the person tested or concerning the required test are provided on the support element used as a main body, in particular on the main body of a test card.

In this context, it is conceivable that one side of a test card carries information concerning the patient and the side carries information concerning the test to be carried out. This spatial separation of the information reliably ensures that confusion is avoided and the corresponding cards can be read out comparatively quickly in the laboratory. Insofar as information fields are provided on the test card for displaying information, they may optionally be designed as written fields and/or as fields that contain other information, mainly codes in the form of barcodes, 3D codes or data matrix codes.

Of course, it is likewise conceivable that the test card is provided with suitable fields making it possible, for example with the aid of crosses or other marks, to make specific selections, for example concerning the required tests.

Preferably, the support element comprises at least one layer of an elastomer, i.e. of a plastic which, by the action of a force, in particular by bending, can be reversibly deformed for a short time, but not permanently, up to a certain limit, and thereafter, in the absence of the action of the force, once again adopts its original shape. Preferably, the support element is composed of an elastomer. The support element preferably serves as a main body for the application of all the elements of a test card comprising the sorption element and overflow reservoir.

The support element is preferably denser than paper and preferably contains sufficient plastic, most preferably elastomer, to ensure that it does not float on the surface of an aqueous reaction solution but instead makes contact via both sides with the aqueous phase, at least after brief shaking or single submersion. This facilitates or in fact permits the transfer of diagnostically relevant substances from a sample, applied on the sorption element, into the aqueous phase.

Particularly preferably, the sorption element is designed in such a way that, in the area of three outer surfaces which lie in different planes, it does not adjoin the support element or the overflow reservoir and, instead, these surfaces face freely toward the outside. In this context, it is conceivable that the sorption element either protrudes outward from the actual test card in the form of a projecting element or is instead arranged inside specifically provided recesses of the test card. In each case, however, the sorption element is arranged in such a way that it can be grasped or pressed comparatively easily by hand and can thus be broken off from the support element and/or the overflow reservoir of the test card, particularly by virtue of the fact that it is connected to the support element via a connection piece that has the predetermined breaking point, said connection piece preferably having a width which is less than the width of the sorption element at its widest point, preferably by at least 10, 20, 30, 40, 50, 75 or 90% of the widest point of the sorption element. The sorption element is preferably circular, i.e. the widest point corresponds to its diameter. The breaking off does not require the use of tools, in particular a punch.

According to a further particular embodiment, the sorption element and/or the overflow reservoir has a filter paper. The filter paper used for the sorption element and/or the overflow reservoir is preferably filter paper from Ahlstrom Filtration LLC, namely Ahlstrom 226 specimen collection paper with FDA approval number K 062932 or Whatman 903 filter paper from GE healthcare with the FDA approval number K932661. The diameter of the sorption element is preferably 4.5 to 5.5 mm, in particular 5 mm. The preferred filling volume is in the range of 3.3 to 4.3 µl, in particular 3.5 µl.

As an alternative or in addition to the use of a filter paper, it is conceivable to use fiber material for the sorption element and/or the overflow reservoir. When a special filter material is used, it is designed in such a way that it easily takes up the drop of sample material, in particular blood, and such that, starting from the center point of the sorption element, a uniformly saturated filling is obtained, such that the sample material can easily be removed from the sorption element in the laboratory, in particular without material losses. Preferred fiber materials are two-component materials of polyamide (better known as nylon) and polypropylene (PP). The corresponding fiber mixes are characterized especially by their absorption properties and the above-described ability by which material that has been absorbed can be released again more or less without loss. According to a very particular embodiment of the invention, the sorption element containing a suitable fiber material has a thickness of 0.4 to 1 mm, in particular of 0.45 mm, wherein the fiber material has a density of 0.3 to 0.4 g/cm$^3$, in particular of 0.33 or 0.37 g/cm$^3$.

In addition to the described device, the invention further relates to a method for transporting a bodily fluid sample from a sampling site to a test site, in particular to a laboratory. In the method a drop of the bodily fluid is dropped onto a sorption element, which is secured on a support element of a test device, in particular in the form of a card. An excess amount beyond the defined amount of bodily fluid required for the test is automatically sucked up by an overflow reservoir adjacent to the sorption element. Thereafter, the test device is brought to the site of the test, in particular to a laboratory, at which test site the sorption element with the bodily fluid sample is detached from the support element of the test device. The method according to the invention is characterized in that the sorption element is broken off from the support element and/or from the overflow reservoir manually, i.e. exclusively by hand. The use of an additional tool, for example a punch, is not necessary when using the method according to the invention.

A particular advantage of the present invention is that the detached sorption element, preferably with a blood sample, more preferably a dried blood sample, can then be used directly for laboratory tests. In a preferred embodiment, the method according to the invention therefore moreover comprises the step of introducing the detached sorption element into an aqueous reaction solution which optionally comprises an antigen that can be used diagnostically. Laboratory tests of this kind can in particular include an immunoassay, in which a sample is dissolved in an aqueous reaction buffer, wherein substances contained therein enter the aqueous phase. Of particular note in this context are diagnostically informative antibodies, for example against infectious diseases such as pathogenic bacteria, viruses or parasites, or auto-antibodies. The aqueous reaction solution thus obtained can, for the purpose of an ELISA, be brought into contact with an antigen preferably immobilized on a solid phase, for example the bottom of a reaction vessel, a substrate or a bead. An antigen/(auto)antibody complex can then be detected by a suitable means, e.g. with a secondary antibody which is tagged with a label, e.g. an enzyme, a radioactive isotope, a fluorescent chemical group or the like. A test of the aqueous solution by means of indirect fluorescence or by contact of a biochip is also possible. Further diagnostic methods besides immunoassays and immunofluorescence include diagnostic nucleic acid amplification by means of PCR. Suitable reagents, including antigens and secondary antibodies, are known to those skilled in the art and are commercially available.

In the course of such a method according to the invention, a sorption element is obtainable by applying a liquid sample, preferably a liquid whole-blood sample, to a sorption element of the device as claimed in one of claims 1 through 8, followed by the steps of breaking off the sorption element and optionally drying the sample.

According to the invention, a broken off sorption element of this kind can be introduced into an aqueous reaction solution which comprises the sorption element according to the invention, optionally in addition to an antigen that can be used diagnostically. It can introduced by simple addition, but also by submersion in the reaction solution and/or by agitation. The conditions are chosen such that soluble substances contained in the sample can transfer into the aqueous reaction solution.

According to the invention, an aqueous reaction solution of this kind is located in a reaction vessel that is suitable for carrying out a diagnostic procedure, for example in a microtiter plate comprising numerous wells, preferably at least or more than 2, 4, 6, 8, 10, 12, 18, 24 or 48 wells, which are suitable for parallel processing of the same number of samples. The size and shape of the sorption element can be adapted to the shape of the wells.

Without limiting the general inventive concept, the invention is described below on the basis of illustrative embodiments and with reference to various figures, in which:

FIG. 3 shows a test card with an area which can be punched out and in which inner sorption elements are arranged, and FIG. 4 shows a detailed view of the overflow reservoir with the sorption elements secured thereon.

Figure 1:
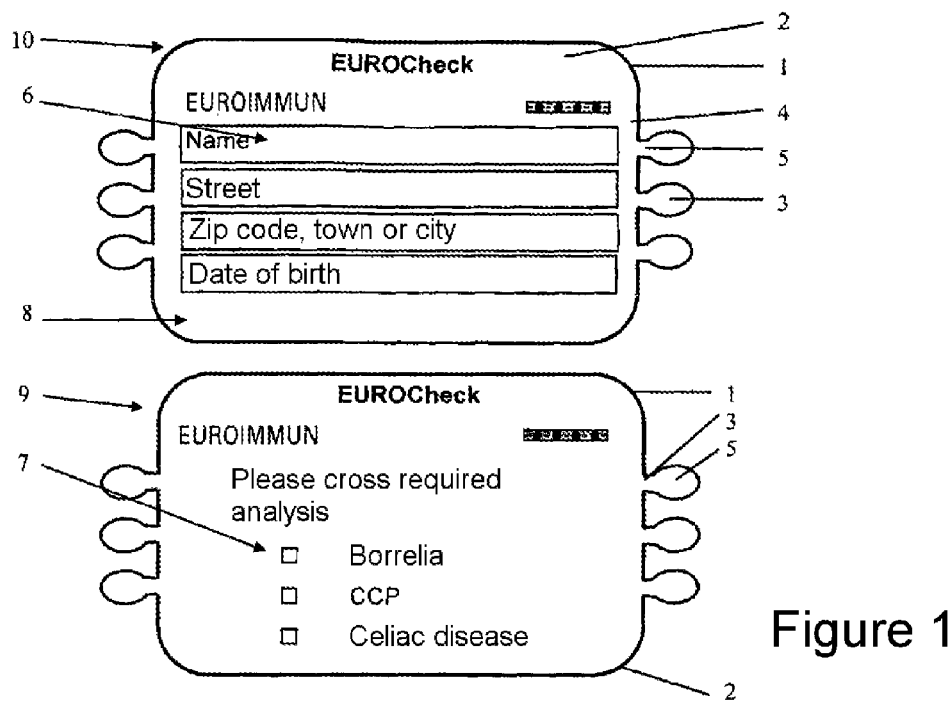
FIG. 1 shows a test card for a dry blood test (dry blot test) with outwardly protruding sorption elements.

FIG. 1 shows a test card designed according to the invention for preferably transporting a patient's blood samples in dried form from the sampling site to a laboratory. The test card 1 shown principally has a support element 2 on the two short sides of which an overflow reservoir 4 and three sorption elements 3 are arranged respectively. Predetermined breaking points 5 are provided between the sorption elements 3, provided on both sides of the test card 1, and the respective common overflow reservoirs 4, such that the sorption elements 3 can be easily removed from the actual test card 1 by breaking them off. A tool is not necessary for this purpose. In this way, a blood sample can be taken by simple means, for example in a medical practice, on a hospital ward, in a pharmacy or even at home, by a drop of blood being dropped onto at least one of the sorption elements, and the card is finally sent to a laboratory for evaluation.

To transport a test card 1, a test card sleeve is advantageously provided into which the test card 1 can be inserted completely, in particular with its sorption elements 3. It is in this way ensured that the test card 1 can be dispatched and transported without damage occurring, in particular to the sorption elements 3, or without the sorption elements being inadvertently broken off too early.

The sorption elements 3 are fiber pads or filter pads with a defined volume for taking up the amount of blood needed for the test evaluation. The sorption elements 3 are adjoined on both sides by an overflow reservoir 4, which has the same material as the sorption elements 3 and which automatically sucks up excess blood that could not be taken up by the sorption element 3. The overflow reservoirs 4 are in this case provided likewise on both short sides of the test card 1, directly on the support element 2, and thus constitute the connection between the support element 2 of the test card 1 and the individual sorption elements 3, of which there are three on each side in the illustrative embodiment shown.

As soon as a test card provided with the corresponding blood samples has arrived at the laboratory, the individual sorption elements 3, which are provided with a blood sample, can be detached in a comparatively simple way by being broken off from the test card 1. A punch is not necessary for this purpose. Furthermore, in order to always ensure a reliable attribution of a blood sample to a patient, the test card 1 shown in FIG. 1 has on one side, namely the rear face 10 of the test card, a total of four information fields 6 which are arranged over one another and into which the name, address and date of birth of the patient can be entered. Moreover, in the lower area, there is an information field 8 into which the expiration date, the batch reference and an order number are entered.

On the side opposite this, i.e. on the front face 9 of the test card 1, there is a further information field 7 with three boxes arranged over one another, in which a cross can be entered for the required test. In the illustrative embodiment shown, it is possible to choose whether a test should be carried out in relation to a medical condition of the patient with borreliosis, rheumatoid arthritis and/or celiac disease.

Moreover, in the upper area of the front face 9 of the test card 1, sufficient space is provided to be able to enter the manufacturer's product names, while further information concerning the manufacturer itself and, for example, the storage of the test card 1 can be indicated in the lower area.

The provision of defined surfaces with filter pads or fiber pads as sorption elements 3 and an adjoining overflow reservoir 4 ensures that very small amounts of blood can be sampled in a simple and convenient manner. In addition, simple transport and defined dosing of a patient sample for later analysis in the laboratory is ensured. The filter pads or fiber pads are each defined by their geometric shape and are secured on the overflow reservoir 4 via a connection with a predetermined breaking point 5. By means of the predetermined breaking point 5, which is preferably designed as a perforation or notch, the actual sorption element 3 required can be detached from the overflow reservoir easily and without using a tool. Thus, with the aid of the test card 1 shown, a patient blood sample kit is preferably to be made available for the physician, the pharmacist or the actual patient, wherein the test card 1 can be reliably dispatched for subsequent use in the diagnostics laboratory.

The simple handling of the test card 1 is in particular ensured by the fact that the card preferably has the format of a check card. The test card 1 shown in FIG. 1 measures 86 mm by 54 mm, and the overflow reservoirs provided on both short sides have a width of approximately 5 mm. The individual sorption elements 3 are arranged at a distance of approximately 4 mm from one another and, parallel to the end edge of the test card 1, have a width of ca. 5 mm.

Figure 2:
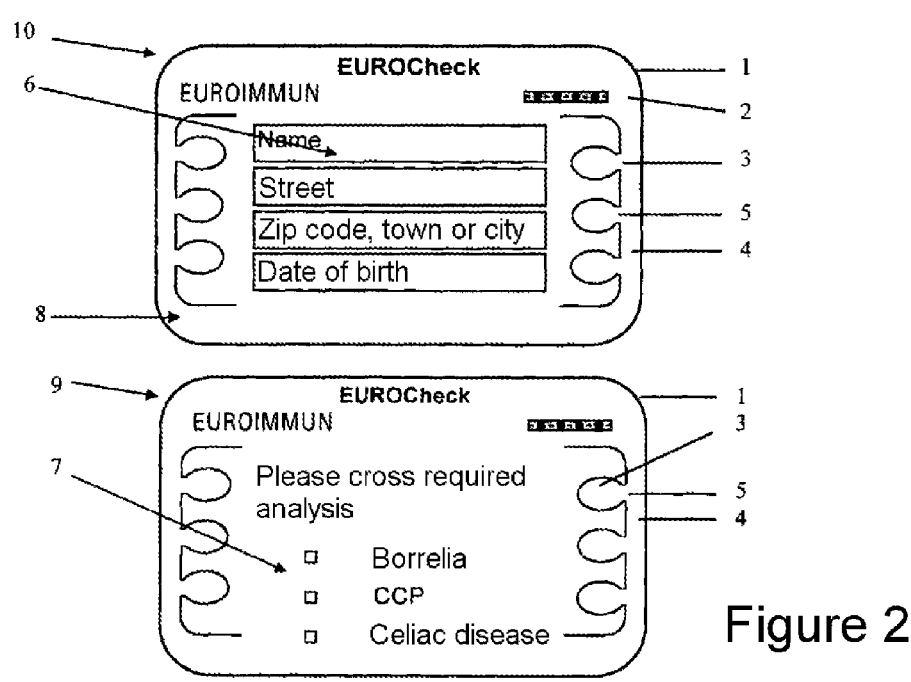
FIG. 2 shows a test card for a dry blood test with sorption elements lying on the inside.
Figure 5:
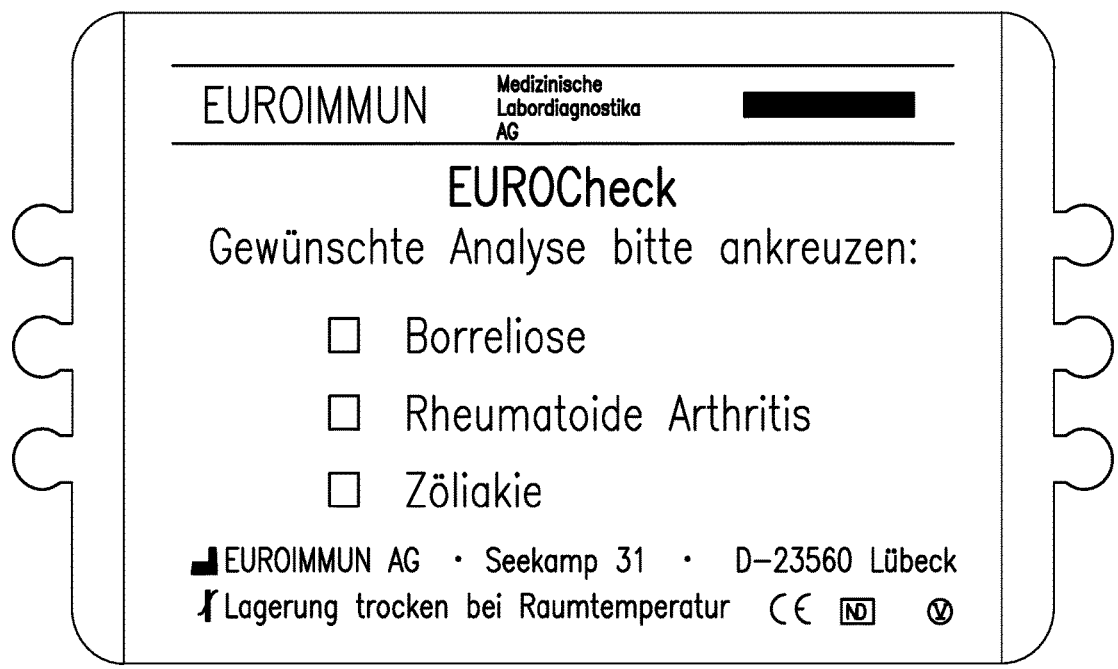
FIG. 5 shows a photograph of a particularly preferred embodiment according to the invention.

FIG. 2, as a supplement to FIG. 1, shows a test card 1 which is designed according to the invention and in which the sorption elements 3 are not in the form of outwardly protruding projections but instead extend inward into a larger recess of the test card 1. The test card 1 once again has a support element 2 on which two overflow reservoirs 4 are secured, each again with three sorption elements 3. An important feature here is that predetermined breaking points 5 are provided between the sorption elements 3, designed as filter pads or fiber pads, and the overflow reservoirs 4. These predetermined breaking points 5 in the form of a perforation or notch allow the sorption elements 3 to be easily broken away from or out of the test card 1. Moreover, the test card 1 once again has, on its front face 9, an information field 7 which permits the selection of the required test, while information fields 6 permitting identification of the patient are provided on the rear face 10.

By way of comparison with the technical solutions explained above, FIG. 3 shows an alternative embodiment of a test card 1 according to the invention. The test card 1 shown in FIG. 3 once again has a front face 9 and rear face 10, wherein the required test can be crossed on the front face 9 and the name, address and date of birth of the patient can be entered on the rear face 10.

In this case, only one overflow reservoir 4 is provided on the test card 1 and is connected to a total of six sorption elements 3. Excess sample material that can no longer be taken up in the filling volume of the respective sorption element 3 is once again adsorbed by the overflow reservoir 4.

In this case too, predetermined breaking points 5 are located between the individual sorption elements 3 and the overflow reservoir 4. This ensures that, in the laboratory, the individual sorption elements 3 can be removed from the test card 1, in particular from the overflow reservoir 4 and the support element 2, by being simply pushed out without using a tool.

FIG. 4 shows, in a schematic detail, the arrangement of an overflow reservoir 4 with sorption elements 3 secured thereon. In principle, it is unimportant in this case whether the sorption elements 3 are sorption elements 3 lying on the outside or on the inside with respect to the test card 1. The important feature is that the overflow reservoir 4 is made from the same material as the filter pads or fiber pads designed as sorption elements 3, i.e. in particular that the same material is used.

The overflow reservoir 4 is designed in such a way, and connected to the sorption elements 3 in such a way, that, during the introduction of a blood sample into a sorption element 3, excess blood, i.e. the amount of a blood sample that exceeds the defined filling volume of a filter pad or fiber pad, is sucked up automatically by the overflow reservoir 4. Suitable predetermined breaking points 5 are once again provided between the sorption elements 3 and the overflow reservoir 4. Predetermined breaking points 5 of this kind are produced by individual holes, or a perforation, or also by notches in the connection area between the sorption elements 3 and the overflow reservoir 4. This measure ensures that the individual sorption elements 3 can be broken off from the overflow reservoir 4 without using a tool. It is expressly stated that it is of course only those sorption elements 3 having a blood sample to be tested that are removed from the respective overflow reservoir 4 or from the test card 1.

LIST OF REFERENCE SIGNS 1 test card
2 support element
3 sorption element
4 overflow reservoir
5 predetermined breaking point
6 information field for sample-specific data
7 information field for test-specific data
8 information field for data specific to the test card
9 front face of the test card
10 rear face of the test card
11 connection piece

The invention claimed is:

1. A device for storing and transporting a bodily fluid sample, comprising:
   a support element,
   at least two sorption elements that each have a perimeter,
   a common overflow reservoir, and
   at least one predetermined breaking point that connects a first portion of the perimeter of a sorption element of the at least two sorption elements to the support element and the overflow reservoir, a second portion of the perimeter of the sorption element being separated from the support element and the overflow reservoir, the first portion of the perimeter having a width that is less than a width of the sorption element at the widest point of the sorption element,
   wherein the support element forms a main body,
   the at least two sorption elements are secured on the support element, have a defined filling volume, and, in use, receive a drop of the bodily fluid,
   the overflow reservoir is adjacent to the at least two sorption elements, and takes up bodily fluid from the sorption element as soon as the filling volume of the sorption element is filled, wherein each sorption element is connected to the common overflow reservoir, and
   the at least one predetermined breaking point is designed in such a way that the sorption element can be manually detached from the support element and from the overflow reservoir without an auxiliary tool.

2. The device as claimed in claim 1, wherein the at least one predetermined breaking point is located between the overflow reservoir and the sorption element.

3. The device as claimed in claim 1, wherein the support element has an information field for entering information concerning the nature and/or origin of the bodily fluid sample and/or concerning a test to be carried out.

4. The device as claimed in claim 3, wherein that the support element has, on a first side, an information field for entering information concerning the nature and/or origin of the bodily fluid sample, and on a second side opposite the first side, an information field for entering information concerning the test to be carried out.

5. The device as claimed in claim 1, wherein the sorption element has at least three surface areas exposed to an environment and arranged in different planes.

6. The device as claimed in claim 1, wherein the sorption element and/or the overflow reservoir has a filter paper.

7. The device as claimed in claim 1, wherein the sorption element and/or the overflow reservoir has at least one material containing fibers.

8. A method for transporting a bodily fluid sample from a sampling site to a test site, the method comprising:
   dropping a drop of the bodily fluid sampled onto a sorption element of a device comprising:

a support element,
at least two sorption elements comprising the sorption element, each of the at least two sorption elements having a perimeter,
a common overflow reservoir, and
at least one predetermined breaking point that connects a first portion of the perimeter of a sorption element of the at least two sorption elements to the support element and the overflow reservoir, a second portion of the perimeter of the sorption element being separated from the support element and the overflow reservoir, the first portion of the perimeter having a width that is less than a width of the sorption element at the widest point of the sorption element,
wherein the support element forms a main body,
the at least two sorption elements are secured on the support element, have a defined filling volume, and, in use, receive a drop of the bodily fluid,
the overflow reservoir is adjacent to the at least two sorption elements, and takes up bodily fluid from the sorption element as soon as the filling volume of the sorption element is filled, wherein each sorption element is connected to the common overflow reservoir, and
the at least one predetermined breaking point is designed in such a way that the sorption element can be manually detached from the support element and from the overflow reservoir without an auxiliary tool.
bringing the device to the test site, and
manually detaching the sorption element with the bodily fluid sample from the support element of the device and the overflow reservoir at the test site.

9. The method as claimed in claim 8, further comprising the step of introducing the detached sorption element into an aqueous reaction solution optionally comprising an antigen that can be used diagnostically.

10. The device of claim 1, wherein the at least two sorption elements each have a first side and a second side, wherein the first is coupled to the overflow reservoir by the at least one predetermined breaking point, wherein the second side extends away from the overflow reservoir.

11. The device of claim 1, wherein the at least two sorption elements extend from a side surface of the overflow reservoir.

12. The device of claim 11, wherein the at least two sorption elements extend away from a side of the support element.

13. The device of claim 1, wherein the device comprises at least two predetermined breaking points, and wherein each sorption element of the at least two sorption elements is separated from the common overflow reservoir by a respective predetermined breaking point of the at least two predetermined breaking points, wherein each sorption element of the at least two sorption elements can be individually manually detached from the support element and from the overflow reservoir without an auxiliary tool.

14. A device for storing and transporting a bodily fluid sample, comprising:
a support element having a perimeter,
at least two sorption elements that protrude from the perimeter of the support element,
a common overflow reservoir, and
at least one predetermined breaking point,
wherein the support element forms a main body,
the at least two sorption elements are secured on the support element, have a defined filling volume, and, in use, receive a drop of the bodily fluid,
the overflow reservoir is adjacent to the at least two sorption elements, and takes up bodily fluid from the sorption element as soon as the filling volume of the sorption element is filled, wherein each sorption element is connected to the common overflow reservoir, and
the at least one predetermined breaking point is designed in such a way that the sorption element can be manually detached from the support element and from the overflow reservoir without an auxiliary tool.

15. The device as claimed in claim 14, wherein the sorption element and/or the overflow reservoir has a filter paper.

16. The device as claimed in claim 14, wherein the sorption element and/or the overflow reservoir has at least one material containing fibers.

* * * * *